(12) United States Patent  
Schrag

(10) Patent No.: US 7,572,218 B2  
(45) Date of Patent: Aug. 11, 2009

(54) IMPLANTABLE MUSCLE CLOSING PROSTHESIS SYSTEM, IN PARTICULAR IN THE ANAL CHANNEL AREA

(75) Inventor: Hans-Jurgen Schrag, Friedenweller (DE)

(73) Assignee: Universitatsklinikum Freiburg, Freiburg (DE)

( * ) Notice: Subject to any disclaimer, the term of this patent is extended or adjusted under 35 U.S.C. 154(b) by 0 days.

(21) Appl. No.: 11/578,346

(22) PCT Filed: Apr. 12, 2005

(86) PCT No.: PCT/DE2005/000640

§ 371 (c)(1),
(2), (4) Date: Oct. 12, 2006

(87) PCT Pub. No.: WO2005/099618

PCT Pub. Date: Oct. 27, 2005

(65) Prior Publication Data

US 2007/0213580 A1    Sep. 13, 2007

(30) Foreign Application Priority Data

Apr. 15, 2004   (DE) ...................... 10 2004 018 807

(51) Int. Cl.
*A61F 2/02* (2006.01)
(52) U.S. Cl. ...................................................... 600/31
(58) Field of Classification Search ............. 600/29–32, 600/37; 128/897–899; 623/23.65, 23.66, 623/23.67
See application file for complete search history.

(56) References Cited

U.S. PATENT DOCUMENTS

| | | | | |
|---|---|---|---|---|
| 4,878,889 A | * | 11/1989 | Polyak | 600/31 |
| 5,509,888 A | | 4/1996 | Miller | |
| 6,432,038 B1 | * | 8/2002 | Bakane | 600/29 |
| 6,461,292 B1 | * | 10/2002 | Forsell | 600/31 |
| 6,491,623 B2 | * | 12/2002 | Snyder et al. | 600/31 |
| 6,805,662 B2 | * | 10/2004 | Shah et al. | 600/29 |
| 6,953,429 B2 | * | 10/2005 | Forsell | 600/29 |
| 7,235,044 B2 | * | 6/2007 | Forsell | 600/29 |

FOREIGN PATENT DOCUMENTS

| | | |
|---|---|---|
| DE | 1973292 | 11/1967 |
| DE | 90 10 783.7 | 10/1990 |
| DE | 100 23 634 | 10/2002 |
| DE | 100 23 634 | 6/2003 |
| EP | 0202815 | 11/1986 |
| EP | 0348114 | 12/1989 |

* cited by examiner

*Primary Examiner*—Charles A Marmor, II
*Assistant Examiner*—Christine D Hopkins
(74) *Attorney, Agent, or Firm*—Antonelli, Terry, Stout & Kraus, LLP.

(57) ABSTRACT

An implantable muscle closing prosthesis system, particularly for opening and closing the rectum, characterized in that it has a compression unit, which comprises a compression cuff (1) and a reservoir cuff (2) molded as hollow bodies, and may integrate a bidirectional micropump (4) of arbitrary construction via a support ring (3), the cuffs primarily being subjected to a material compression during the inflation and deflation and communicating with one another via the micropump (4), which may be activated using a separate control unit, or is also manually operable from the outside.

18 Claims, 1 Drawing Sheet

IMPLANTABLE MUSCLE CLOSING PROSTHESIS SYSTEM, IN PARTICULAR IN THE ANAL CHANNEL AREA

BACKGROUND OF THE INVENTION

1. Field of the Invention

The present invention relates to an improved, implantable sphincter prosthesis system for treatment of high-grade stool incontinence, which may be implanted in a space-saving way around the anal channel due to its highly integrated conception.

2. Description of the Prior Art

The currently clinically relevant Acticon Neosphincter, which is described in the literature, for treating high-grade stool incontinence comprises three separate functional components to be implanted in different anatomical areas: an inflatable ring to be adjusted around the intestine like a collar, which compresses the anal channel, a separate pressure accumulator for the compression medium, and a unidirectional pump, which connects the two components and pumps the compression medium out of the compression collar back into the pressure accumulator (Wong W D, et al., Disease of Colon and Rectum 2002, 9:1139-1153). The configuration of the functional components requires complex surgery and results in complication and explantation rates around 40%. A more compact muscle closing device, in which a change of the viscosity and density of a colloidal magnetorheological liquid is exploited for the compression procedure (U.S. Pat. No. 5,509,888), is without clinical relevance up to this point. Various devices comprising multiple seal elements which move peristaltically for closing an end of the intestine (DE 100 23 634 C2; DE 197 32 92 A1) are not usable in the area of the anal channel and thus differ significantly from the present invention, as do the systems for closing the urethra (DE 90 10 783 U1; EP 02 02 815 A2; EP 03 48 114 A1) known from urology.

Furthermore, the compression collars described in the literature are highly elastic inflatable bodies, which are essentially subject to an expansion in the scope of the inflation or deflation (balloon principle). Achieving a circular, symmetrical, and efficient lumen compression using extremely small volumes against high pressures, as may occur in the scope of efficient continence compression in the area of the anal channel, is subjected to narrow limits because of the strong deformation of the inflatable bodies. In addition, the high pressure gradient already existing at the beginning in the inflatable bodies influences the performance spectrum of a micropump, which is employed, extremely negatively during the inflation.

SUMMARY OF THE INVENTION

The invention thus relates to a muscle closing prosthesis for voluntarily achieving stool continence or defecation, which, because of its unique compact construction and function may be implanted in a significantly simplified way perianally, over the sphincter ani externus muscle in the area of the anal channel, or conventionally, using laparotomy or laparoscopy at the level of the inferior pelvic aperture, and integrates all components necessary for its function.

The present invention includes a compression unit comprising: a special compression cuff formed as a hollow body on an interior of an elastic support ring, on whose exterior a reservoir cuff for the compression medium is located. The compression cuff and reservoir cuff communicate via a bidirectional micropump of suitable construction (based on piezo technology, for example) which is integrated in the support ring or attached thereto, and via transmission lines which are completely or partially integrated into the ring.

All surfaces comprise one or a combination of multiple different biocompatible and/or physiologically inert materials (such as polyurethane, titanium) isotonic sodium chloride solution or oils compatible with the body being able to be used as transmission fluids or a gas or gas mixture, for example, air, being able to be used as transmission media.

BRIEF DESCRIPTION OF THE DRAWINGS

The function and further advantages of the muscle closing prosthesis are explained by the embodiment description on the basis of FIG. 1.

REFERENCE NUMERALS

Figure 1:
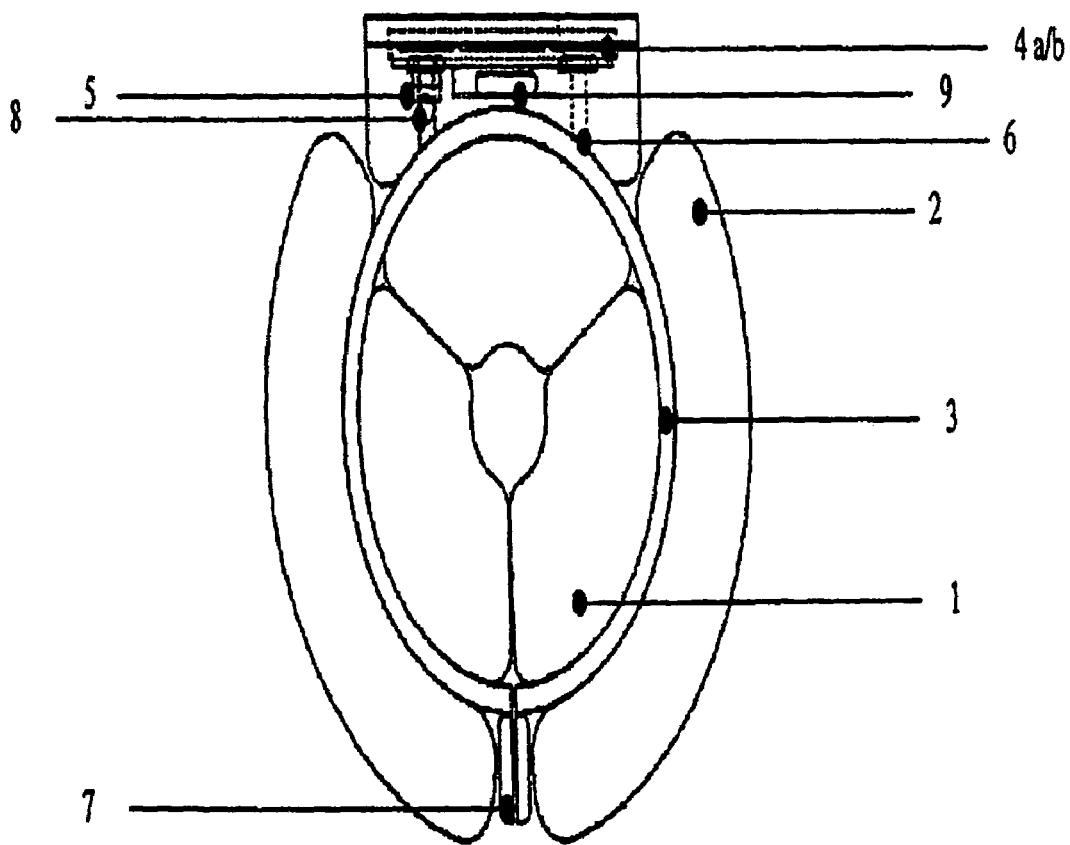

1 compression cuff
2 reservoir cuff
3 support ring
4 micropump
4a/b shutoff valves
5 pressure sensor
6 transmission line
7 quick-acting closure
8 port
9 terminal for external power source/control electronics

DETAILED DESCRIPTION OF THE INVENTION

In detail, FIG. 1 shows the complete compression unit in section, having compression cuff (1), and reservoir cuff (2), support ring (3), and integrated micropump (4). The molded hollow bodies of the compression and reservoir cuffs are shown in a non-evacuated, or inflated state. The compression cuff (1) is shown in a concave, three-chamber embodiment.

The use of a bidirectional micropump (4) having integrated shutoff valves (4a/b), implemented in FIG. 1 as a piezo pump, allows the reduction of the large pressure equalization or reservoir container to be implanted separately, which was typical in the prior art until now. The volume solely has to correspond to the compression volume in this way, so that the reservoir cuff (2) may be attached to the exterior of the support ring (3).

A further innovation is the embodiment of the compression cuff (1) and reservoir cuff (2), which are manufactured as hollow bodies, which may be evacuated, made of polyurethane, for example, which is outstandingly suitable for this purpose. The inflation or deflation is based primarily on a material compression and deformation of a hollow body having defined volume at largely constant wall thickness and not on a material expansion, as is normal in the typical compression bodies manufactured from silicone, for example.

In addition to the lower material strain, the advantage is the elimination of the initial expansion resistance of the compression cuff (1), from which a hysteresis phenomenon of the intra-cuff pressure during the compression filling is derived. This, in combination with the minimal dead space volume of the transmission lines (6) resulting from the integrated system, has a positive effect on the performance characteristic and the energy management of the micropump (4) to be used.

The support ring (3), and the cuffs (1, 2) which are attached on both sides (ideally manufactured from polyurethane), allow the opening of the ring for implantation by 180°. The ring may be mechanically or electromagnetically closed by a quick-acting closure (7).

After implantation of the prosthesis having primary evacuated cuffs, the reservoir cuff (2) is filled via the port (8). The activation of the micropump (4) causes the filling of the compression cuff (1) from the reservoir cuff (2) via the integrated transmission lines (6). The closure of the anal channel is produced (continence performance).

A reversal of the fluid or air transmission causes the emptying of the compression cuff (1) (defecation). The integrated pressure sensor (5) allows a tissue-protective pressure regulation and is additionally usable as an indicator for an imminent defecation (increase of the intra-cuff pressure in the event of waiting stool column). A separate patient programming unit is used for voluntary activation of the continence performance or defecation (function on/off, or pressure/volume adapted regulation as a function of the stool consistency and within a pressure range predefined by the physician). In this case, a subcutaneously implanted receiver is activated telemetrically or by radio, for example, using the patient programming unit, the receiver being connected via a cable connection by suitable terminals (9) to the sphincter prosthesis. The activation may also be performed using a radio remote-control module integrated in the prosthesis, through which the functional components are reduced by the subcutaneous receiver and the cable connection.

The invention claimed is:

1. An implantable muscle closing prosthesis system for opening and closing an anal channel or a hollow organ segment, comprising an elastic compression cuff including a hollow body for containing a fluid subject to evacuation, and being located on an interior of an elastic support ring, an elastic reservoir cuff including a hollow body for containing the fluid subject to evacuation, a micropump coupling the elastic compression cuff to the elastic reservoir cuff to provide flow of the fluid therebetween and the hollow body of the elastic reservoir cuff including a port for the evacuation of the fluid and being attached to an exterior of the support ring, the fluid being injectable into the elastic reservoir cuff, the micropump being activated by an external device; and wherein the compression cuff and the elastic reservoir cuff provide compression and deformation of the hollow bodies without expansion of walls of the hollow bodies while a wall thickness of the hollow bodies is substantially constant.

2. The muscle closing prosthesis system according to claim 1, wherein the compression cuff includes a concave or convex surface facing toward the anal channel or the hollow organ segment to be compressed and comprises connected chambers, the chambers being filled simultaneously or in a delayed chronological sequence, symmetrically or asymmetrically relative to one another, to compress the anal channel or the hollow organ segment circularly.

3. The muscle closing prosthesis system according to claim 2 wherein the micropump is activated magnetically, telemetrically or by an induction coil and the external device is a programming device.

4. The muscle closing prosthesis system according to claim 1, comprising a fixed, soft buttress and wherein the compression cuff has a concave or convex surface facing toward the anal channel or the hollow organ segment to be compressed and comprises connected chambers, so that the anal channel or the hollow organ segment is compressed against the fixed, soft buttress, to provide closure.

5. The muscle closing prosthesis system according to claim 4 wherein the micropump is activated magnetically, telemetrically or by an induction coil and the external device is a programming device.

6. The muscle closing prosthesis system according to claim 1, comprising elastic, compressible filler cushions within the compression cuff providing reduction of compression volume inside the compression cuff.

7. The muscle closing prosthesis system according to claim 6 wherein the micropump is activated magnetically, telemetrically or by an induction coil and the external device is a programming device.

8. The muscle closing prosthesis system according to claim 1, where the reservoir cuff comprises hollow chambers in fluid connection to one another.

9. The muscle closing prosthesis system according to claim 8 wherein the micropump is activated magnetically, telemetrically or by an induction coil and the external device is a programming device.

10. The muscle closing prosthesis system according to claim 1, wherein the elastic reservoir cuff includes a tissue expander comprising a flexible envelope connected to the support ring, which is not in fluid connection to the hollow body of the support ring.

11. The muscle closing prosthesis system according to claim 10 wherein the micropump is activated magnetically, telemetrically or by an induction coil and the external device is a programming device.

12. The muscle closing prosthesis system according to claim 1, wherein at least one valve blocks transmission of the fluid between the compression cuff and the reservoir cuff which is integrated into the micropump.

13. The muscle closing prosthesis system according to claim 12 wherein the micropump is activated magnetically, telemetrically or by an induction coil and the external device is a programming device.

14. The muscle closing prosthesis system according to claim 1, wherein the micropump is separated from the elastic compression cuff, elastic support ring and elastic receiving cuff.

15. The muscle closing prosthesis system according to claim 14 wherein the micropump is activated magnetically, telemetrically or by an induction coil and the external device is a programming device.

16. The muscle closing prosthesis system according to claim 1, wherein the pump pumps the fluid in one direction, from the reservoir cuff into the compression cuff and the compression cuff is emptied passively as a result of an existing pressure gradient between the compression cuff and the evacuated reservoir cuff and pressure exerted by a stool on the compression cuff during the defecation.

17. The muscle closing prosthesis system according to claim 16 wherein the micropump is activated magnetically, telemetrically or by an induction coil and the external device is a programming device.

18. The muscle closing prosthesis system according to claim 1 wherein the micropump is activated magnetically, telemetrically or by an induction coil and the external device is a programming device.

* * * * *